US011724130B2

United States Patent
Lewis, Jr. et al.

(10) Patent No.: US 11,724,130 B2
(45) Date of Patent: Aug. 15, 2023

(54) WEARABLE ULTRASOUND DEVICE

(71) Applicant: ZetrOZ, Inc., Trumbull, CT (US)

(72) Inventors: George K. Lewis, Jr., Trumbull, CT (US); Bryant Guffey, Shelton, CT (US); JoAnne Guarino, Milford, CT (US); Shane Fleshman, Milford, CT (US); Matthew Langer, Shelton, CT (US)

(73) Assignee: ZETROZ SYSTEMS LLC, Trumbull, CT (US)

( * ) Notice: Subject to any disclaimer, the term of this patent is extended or adjusted under 35 U.S.C. 154(b) by 106 days.

(21) Appl. No.: 14/900,000

(22) PCT Filed: Jun. 24, 2014

(86) PCT No.: PCT/US2014/043953
§ 371 (c)(1),
(2) Date: Dec. 18, 2015

(87) PCT Pub. No.: WO2014/210065
PCT Pub. Date: Dec. 31, 2014

(65) Prior Publication Data
US 2016/0136462 A1 May 19, 2016

Related U.S. Application Data

(60) Provisional application No. 61/838,773, filed on Jun. 24, 2013, provisional application No. 61/838,811, filed on Jun. 24, 2013.

(51) Int. Cl.
A61N 7/00 (2006.01)
A61H 23/02 (2006.01)
(Continued)

(52) U.S. Cl.
CPC ........... *A61N 7/00* (2013.01); *A61H 23/0245* (2013.01); *A61B 2017/00106* (2013.01);
(Continued)

(58) Field of Classification Search
CPC ................ A61N 7/00; A61N 2007/006; A61N 2007/0073; A61N 2007/0078;
(Continued)

(56) References Cited

U.S. PATENT DOCUMENTS 6,039,694 A * 3/2000 Larson ................. A61B 8/4281
600/459
9,211,106 B2 * 12/2015 Berard-Andersen .......................
A61B 8/4281
(Continued)

FOREIGN PATENT DOCUMENTS

EP 1812110 B1 6/2013
WO 2010/029556 A1 3/2010
(Continued)

OTHER PUBLICATIONS

European Patent Office, Supplementary European Search Report, issued in European Patent Application No. 14818371, dated Jan. 26, 2017.
(Continued)

*Primary Examiner* — Hien N Nguyen
(74) *Attorney, Agent, or Firm* — FisherBroyles, LLP; Andrew K. Gonsalves, Esq.

(57) ABSTRACT

A wearable ultrasound device and method of using the device includes a power controller with a power source and at least one integrated circuit that delivers electrical power to an applicator. The applicator is electrically coupled to the power controller and a surface of the applicator transmits ultrasound to a wearer for a given duration. The applicator includes radio frequency (RF) drive electronics, an ultra-
(Continued)

sound transducer coupled to the drive electronics, a monitoring apparatus that includes a thermal cutoff coupled to the drive electronics, where the monitoring apparatus monitors a temperature of the applicator surface and the thermal cutoff turns off the applicator, if the temperature exceeds a predefined threshold, and a coupling bandage coupled to the applicator, where the bandage positions the surface of the applicator proximate to a wearer at a location on the body of a wearer.

7 Claims, 14 Drawing Sheets

(51) Int. Cl.
*A61B 17/00* (2006.01)
*A61B 17/225* (2006.01)
*A61B 18/00* (2006.01)

(52) U.S. Cl.
CPC .......... *A61B 2017/2253* (2013.01); *A61B 2018/00791* (2013.01); *A61H 2201/0176* (2013.01); *A61H 2201/0184* (2013.01); *A61H 2201/5015* (2013.01); *A61H 2201/5043* (2013.01); *A61H 2201/5058* (2013.01); *A61H 2201/5097* (2013.01); *A61H 2230/207* (2013.01); *A61H 2230/25* (2013.01); *A61H 2230/505* (2013.01); *A61N 2007/006* (2013.01); *A61N 2007/0073* (2013.01); *A61N 2007/0078* (2013.01)

(58) Field of Classification Search
CPC ........ A61H 23/0245; A61H 2201/0176; A61H 2201/0184; A61H 2201/5015; A61H 2201/5043; A61H 2201/5058; A61H 2201/5097; A61H 2230/207; A61H 2230/25; A61H 2230/505; A61B 2017/00106; A61B 2017/2253; A61B 2018/00791

See application file for complete search history.

(56) References Cited

U.S. PATENT DOCUMENTS

| | | |
|---|---|---|
| 2005/0226921 A1 | 10/2005 | Kortzebom |
| 2006/0184071 A1 | 8/2006 | Klopotek |
| 2007/0208280 A1* | 9/2007 | Talish ...................... A61N 7/00 601/2 |
| 2008/0027359 A1 | 1/2008 | Thierman |
| 2010/0094149 A1 | 4/2010 | Kohut et al. |
| 2010/0324611 A1* | 12/2010 | Deming ............... A43B 3/0005 607/2 |
| 2012/0109018 A1 | 5/2012 | Gertner et al. |
| 2012/0277640 A1 | 11/2012 | Lewis, Jr. et al. |
| 2012/0283605 A1 | 11/2012 | Lewis, Jr. |

FOREIGN PATENT DOCUMENTS

| | | | |
|---|---|---|---|
| WO | WO2011082407 | * | 7/2011 |
| WO | 2011/163570 A2 | | 12/2011 |

OTHER PUBLICATIONS

ISA/KR International Search Report, issued in PCT/US2014/043953, dated Oct. 14, 2014.

* cited by examiner

WEARABLE ULTRASOUND DEVICE

CROSS REFERENCE TO RELATED APPLICATION

The present invention is a U.S. National Phase filing under 35 U.S.C. § 371 of International Application No. PCT/US2014/043953, filed Jun. 24, 2014, and published as WO 2014/210065-A1 on Dec. 31, 2014, which claims benefit of priority from U.S. Provisional Patent Application No. 61/838,773, and U.S. Provisional Patent Application No. 61/838,811. The entire contents of each of the prior applications are incorporated herein by reference in their entirety.

FIELD OF THE INVENTION

The present invention relates to methods of using a wearable ultrasound device, and the wearable ultrasound device.

BACKGROUND OF THE INVENTION

Traditional therapeutic ultrasound generation technologies have a number of deficiencies that prohibit their use in portable ultrasound delivery devices. For example, current therapeutic ultrasound generation technologies are generally, at the smallest, shoebox-sized devices that include a user interface, power generation circuitry, and a separate transducer attached via a hand wand. The devices vary in shape and size, but generally are 6-20 pounds. Such devices also require wall power and administer ultrasound energies from 0-4 Watts and at frequencies of from 1-3 MHz. The energy from the transducers of such devices is applied to penetrate into the tissue and administer ultrasound. Traditional ultrasound therapies are for a short duration (e.g., 5-20 minutes). However, sustained therapy on the body elicits increased biophysical effects on tissue including tissue bioregeneration for accelerated healing, and improved pain management, which is not possible with current devices. Other purported therapeutic ultrasound technologies purport to be portable, but are capable of producing only surface ultrasound waves.

Further, therapeutic ultrasound devices are generally not able to be used for long periods, due to safety concerns, the non-portable size of the devices or the need for external power sources. Thus, among other deficiencies in the art, there is a need for portable therapeutic ultrasound devices that are able to safely deliver ultrasound energy deep into tissue.

SUMMARY OF THE INVENTION

Shortcomings of the prior art are also overcome and additional advantages are provided through a wearable ultrasound device that includes: a power controller comprising a power source and at least one integrated circuit, wherein the power controller delivers electrical power to an applicator; the applicator electrically coupled to the power controller, wherein a surface of the applicator transmits ultrasound to a wearer for a given duration, the applicator comprising: radio frequency (RF) drive electronics; an ultrasound transducer coupled to the drive electronics; a monitoring apparatus comprising a thermal cutoff coupled to the drive electronics, wherein the monitoring apparatus monitors a temperature of the applicator surface and the thermal cutoff turns off the applicator, if the temperature exceeds a pre-defined threshold; and a coupling bandage coupled to the applicator, wherein the bandage positions the surface of the applicator proximate to a wearer at a location on the body of the wearer.

Shortcomings of the prior art are also overcome and additional advantages are provided through a wearable ultrasound device that includes: a power controller comprising a power source and at least one integrated circuit, wherein the power controller delivers electrical power simultaneously to a first applicator and a second applicator; the first applicator electrically coupled to the power controller and the second applicator, wherein a first surface of the first applicator transmits ultrasound to a wearer for a given first duration, the first applicator comprising: first radio frequency (RF) drive electronics; a first ultrasound transducer coupled to the RF drive electronics; a first monitoring apparatus, coupled to the first drive electronics, the first monitoring system comprising a first thermal cutoff, wherein the first monitoring apparatus monitors a temperature of the first applicator surface and the thermal cutoff turns off the first applicator, if the temperature of the first applicator surface exceeds a pre-defined threshold; the second applicator electrically coupled to the power controller, wherein a second surface of the second applicator transmits ultrasound to a wearer for a given second duration, the second applicator comprising: second radio frequency (RF) drive electronics; a second ultrasound transducer coupled to the second drive electronics; a second monitoring apparatus coupled to the drive electronics, the second monitoring system comprising a second thermal cutoff, wherein the second monitoring apparatus monitors a temperature of the second applicator surface and the thermal cutoff turns off the second applicator, if the temperature of the second applicator surface exceeds a pre-defined threshold; and a first coupling bandage coupled to the first applicator, wherein the first bandage positions the first surface proximate to a wearer at a first location on the body of the wearer; and a second coupling bandage coupled to the second applicator, wherein the second bandage positions the second surface proximate to a wearer at a second location on the body of the wearer, wherein the first location and the second location are not the same location.

Shortcomings of the prior art are also overcome and additional advantages are provided through a method of utilizing a wearable ultrasound device that includes: electrically coupling a power controller comprising a power source and at least one integrated circuit, to a first applicator and delivering power to the first applicator, wherein the first applicator comprises RF drive electronics coupled to a transducer, a surface to radiate ultrasound, and a monitoring system comprising a thermal cutoff; coupling a first side of a first bandage to a first location on the body of a wearer, wherein the first bandage comprises a first reservoir of hydrogel, wherein after the coupling, a first portion of the first hydrogel reservoir covers the location; coupling a second side of the first bandage to the first applicator, such that after the coupling a portion of the surface of the first applicator is in contact with a second portion of the first hydrogel reservoir; transmitting ultrasound from the surface of the first applicator through the first reservoir for a pre-determined duration, to the first location; monitoring a temperature of the surface of the first applicator with the monitoring system of the first applicator to determine when the temperature exceeds a pre-defined threshold; and based on the monitoring, modulating the output of the transducer.

Other embodiments and aspects of the invention are described in detail herein and are considered a part of the claimed invention. Other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

DETAILED DESCRIPTION OF THE INVENTION

Embodiments of the present invention include a wearable ultrasound device that can be utilized, for example, for tissue bioregeneration for accelerated healing, and pain management. Embodiments of the present invention include a wearable, long-duration, ultrasonic diathermy device for use in applying deep therapeutic treatment. Embodiments of the present invention include an ultrasound therapy device that can be worn daily, including for time periods exceeding thirty minutes to up to forty-eight hours. In an embodiment of the present invention, the device can be utilized for the aforementioned time period on a single power source charge.

Figure 1:
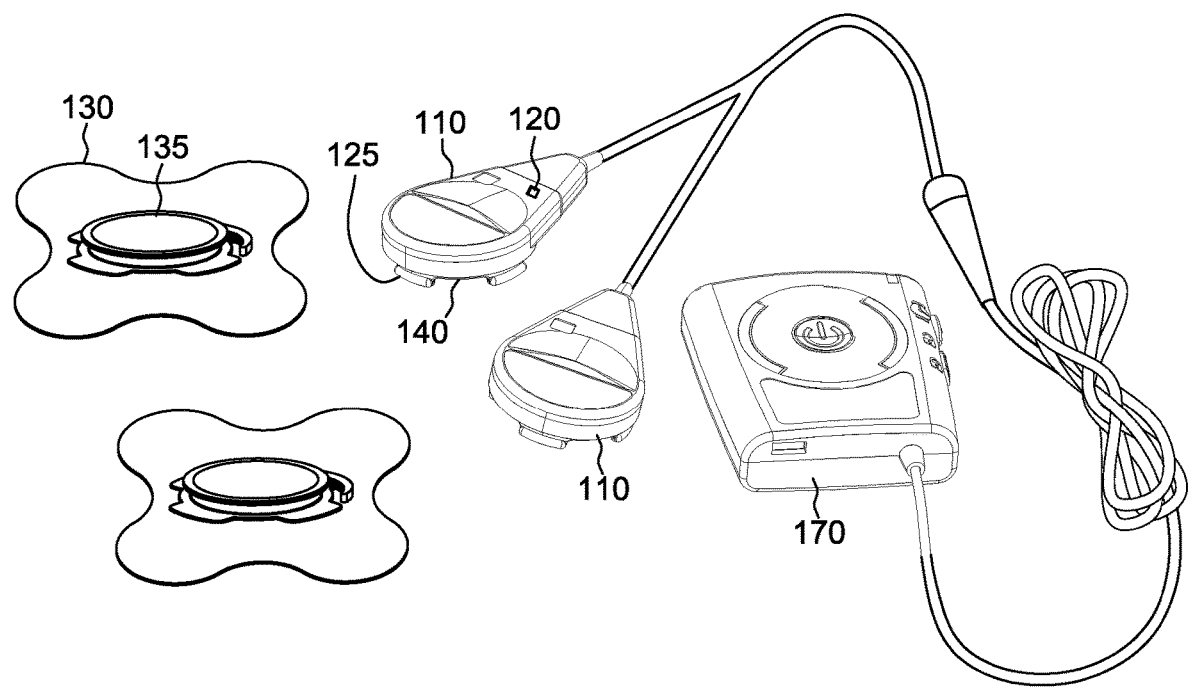
FIG. 1 depicts aspects of an embodiment of the present invention.

Certain embodiments of the present invention include: 1) a power controller (with DC output); 2) an applicator (with integrated RF drive electronics); 3) an ultrasound transducer; 4) closed-loop treatment monitoring apparatus (continuous monitoring capabilities), including a thermal cutoff; and 5) an ultrasound coupling bandage. In some embodiments of the present invention, the bandage is adapted for one time use. FIG. 1 depicts an embodiment of the present invention; the subsequent figures depict aspects of the components of this embodiment, as well as aspects of additional embodiments.

Embodiments of the present invention can be utilized for ultrasound-related applications, including but not limited to, hands-free deep tissue heating and/or soft tissue bioregeneration for accelerated healing. Additionally, embodiments of the present device also take and provide a wearer with biometric measurements, including, but not limited to, blood flow, blood oxygen, mechanical elastography, acoustic spectroscopy, and skin temperature, etc. In embodiments of the present invention, these biometric measurements may be taken by the applicator, the coupling bandage, the controller, and/or an external device. The measurements can be utilized to alter/control the treatment regimen provided by the device. In an embodiment of the present invention, the device may self modulate over the course of a weekly/monthly treatment to improve therapeutic outcome, including but not limited to controlling the dose administered based on biometric feedback.

As seen in FIG. 1, an embodiment of the present invention is a wearable ultrasonic device 100 with at least one applicator 110, an integrated power cutoff temperature sensor, also termed a thermal cutoff 120, an acoustic coupling detector 125, and a coupling bandage 130. In an embodiment of the present invention, the coupling bandage 130 includes an interlocking lip 140, which is built into an applicator housing 160. The interlocking lip 140 couples the applicator 110 with the coupling bandage 130. As explained relative to FIG. 1, in an embodiment of the present invention, the applicator 110, connection lip 140, thermal cutoff 120, acoustic coupling detector 125, and coupling bandage 130, work together with a power controller 170 during the administration of ultrasonic diathermy from the device 100.

Various components of embodiments of the wearable ultrasound device of the present invention will be discussed in more detail later. In general, in an embodiment of the present invention, a power controller with DC output, includes a power source, such as a battery. The power controller 170 provides user control of the device and delivers electrical power to the applicator(s) 110 with controlled, stable amplitude, for a defined period of time. In the applicator 110, with integrated RF drive electronics, drives at least one transducer, in order to transmit ultrasound through a lens. This applicator is positioned to deliver ultrasound to a site of the body of the wearer and a coupling bandage 130 is utilized both to lubricate the surface where the ultrasound will be administered, and to affix the applicator 110 to the treatment site on the body of the wearer. The applicator 110 is connected to the coupling bandage at the applicator 110 housing's interlocking/coupling lip 140. When coupled to the coupling bandage 130, the lens of the applicator 110 contacts a reservoir in the coupling bandage 130 that contains a hydrogel. Thus, the applicator 110 administers ultrasound through this hydrogel reservoir 135 in the bandage 130. This coupling prevents the surface of the radiating ultrasound face of the applicator 110 from coming into contact with the skin of the wearer (e.g., patient) receiving ultrasound.

In an embodiment of the present invention, the coupling bandage 130 has a built-in reservoir filled with a biocompatible hydrogel 135. The hydrogel may be comprised of traditional ultrasound gel, water and polyethylene oxide, which is commonly used in wound healing devices, or other hydrogels, as understood by one of skill in the art. The reservoir of hydrogel reduces the need for the use of traditional ultrasound coupling gel in order to utilize the ultrasound, however, embodiments of the device can utilize this more traditional approach. In an aspect of the present invention, the coupling bandage 130 assists in securing the applicator 110, so that the device can operate in a hands-free mode for up to a multi-hour duration. In an embodiment of the present invention, ultrasound treatments, including but not limited to deep tissue heating (deep tissue diathermy) may be administered by an applicator 110 for thirty minutes or more with no user intervention, and/or in an active or mobile environment.

The thermal cutoff 120 and the acoustic coupling detector 125 are components of the applicator 110 and are configured to de-activate the applicator 110 to stop the ultrasound transmission, if the device 100 functions in a manner that poses a danger to the wearer. In an embodiment of the present invention, the thermal cutoff 120 can be pre-set, for example, during manufacture, to switch the applicator 110 off if the surface contacting the treatment site is of a given heat. In one embodiment of the present invention, the thermal cutoff 120 is configured to cut power to the ultrasound applicator 110 when this temperature meets or exceeds 51° C. In an embodiment of the present invention, a thermal cutoff 120 monitors the patient-contacting surface of the applicator. The thermal cutoff 120 turns off the applicator 110 when the patient-contacting surface exceeds a pre-determined temperature.

Responsive to additional conditions, which will be discussed later, the systems on the applicator 110 can modulate the ultrasound output. Modulating includes, but is not limited to, automatically turning off the applicator utilizing the thermal cutoff, adjusting the frequency of the output, and/or pulsing the ultrasound.

The thermal cutoff 120 is a safety measure, and therefore, the pre-configured temperature point for cut-off should be achieved only when the device is operated in extreme environments or without appropriate coupling. A temperature controller 150 within an embodiment of the device provides an additional level of safety when the device is operational by providing closed-loop continuous ultrasound heating of the body without over heating the tissue to unsafe levels. The thermal cutoff 120 also protects the applicator 110 from overheating and damaging any piezoelectric elements, including but not limited to a crystal element, within the ultrasound applicator 110. A further advantage of the thermal cutoff 120 is that it increases the durability of the device.

In an embodiment of the present invention, the closed-loop monitoring system, which also includes an acoustic coupling detector 125, may also monitor the ultrasound leaving the device (through the applicator 110), the treatment time, and the blood oxygenation, and can make adjustments to the ultrasound treatments based on this monitoring. Additional sensors may be integrated into the applicator 110 in order to enable monitoring of the ultrasound treatment and the wearer/patient. In an embodiment of the present invention, a near infrared sensor is integrated in the applicator 110. In an embodiment of the present invention, the near infrared sensor monitors through an opening in the lens. In another embodiment of the present invention, the sensor window is located in a region on the applicator 110 that is outside the portion of the applicator 110 that attached to the coupling bandage 130.

In an embodiment of the present invention, when the thermal cutoff 120 activates and turns off the applicator 110, for example, when the device is applied improperly or left turned on without being properly acoustically coupled to the body with the coupling bandage 130, an alert to the user can signal the cutoff Alerts include, but are not limited to, a light on the device 100, including both visual, auditory, and other sensory alerts, including but not limited to, vibration. For example, an embodiment of the present invention notifies a user of the activation of the cutoff 120 by illuminating a Light Emitting Diode (LED) error light, and triggering a vibration from the applicator 110. In embodiments of the present invention where an alert can include vibration, the applicator 110 includes a vibration motor (not pictured).

In an embodiment of the present invention where more than one applicator 110 is connected to the power controller 170, the thermal cutoff features of the device may work individually for each applicator 110. For example, an embodiment can include a first applicator and a second applicator that are both coupled to the power controller and are transmitting simultaneously at different location on the body of a wearer. If the thermal cutoff in one of the applicators senses a temperature outside of the pre-configured range, that thermal cutoff will shut off that applicator. Meanwhile, the second applicator can continue operating.

One or more applicators 110 deliver ultrasound to a wearer. An embodiment of the present invention may include more than one applicator 110. The applicators 110 can each be preset to deliver 0.65 W at 3 MHz per applicator 110 (or other frequencies and powers). This embodiment enables the ultrasonic diathermy to be positioned on the body at various treatment locations. Each applicator 110 is positioned with a respective coupling bandage 130. In an embodiment of the present invention when more than one applicator is coupled to the power controller, the applicators can each deliver ultrasound at the same or at different frequencies. In an embodiment of the present invention, an applicator 110 is capable of multimodal operation, i.e., the applicator 110 can transmit ultrasound at two or more frequencies of operation, including but not limited to, frequencies from 20 kHz to 40 MHz The applicator 110 may also operate in different specialized modes. For example, in a sensitive skin mode, the applicator 110 may transmit reduced output power from the transducer and pulse the ultrasonic drive signal or other mechanism to reduce heat accumulation.

In an embodiment of the present invention where more than one applicator 110 is connected to the power controller 170, the applicators can be used together in order to attain a more effective penetration of the body of a wearer, including increasing the surface area that can be treated. For example, two or more applicators 110 can be placed at a position where the ultrasound transmitted from these applicators 110 creates constructive interference as beams overlap and create shear waves. The angle between the applicators contributes to type of transmissions. More than one applicator 110 can be utilized to simultaneously treat a region of the body in order to deliver more energy, but at a low profile on the body of the wearer.

In an embodiment of the present invention, using more than one applicator can increase the therapeutic level of the treatment by multiples. For example, when applying ultrasound to certain parts of the body of a patient, at 1 cm from the application point, the signal is about five times weaker because the ultrasound is exponentially attenuated as it goes into tissue. If two applicators are utilized at a spacing that provides constructive interference, at 1 cm, the signal loss can be cut in half. Thus, utilizing more than one applicator in a manner that created interference between the ultrasound waves being transmitted by each applicator delivers more energy to the wearer. Additionally, using two applicators allows more energy at deeper depths, but allows for less superficial heating than with treating with one higher power applicator.

As mentioned earlier, an applicator 110 administers ultrasound, but also collects information during treatment, utilizing aforementioned monitoring capabilities. In an embodiment of the present invention, an applicator 110 can obtain information including, but not limited to, skin temperature, applicator temperature, pulse oximetry, blood flow, blood oxygen content, mechanical elastography of the tissue, and/or other biometric information. For example, in an embodiment of the present invention, the applicator 110 includes a touch free infrared heat sensor to monitor skin temperature during treatment.

Figure 7:
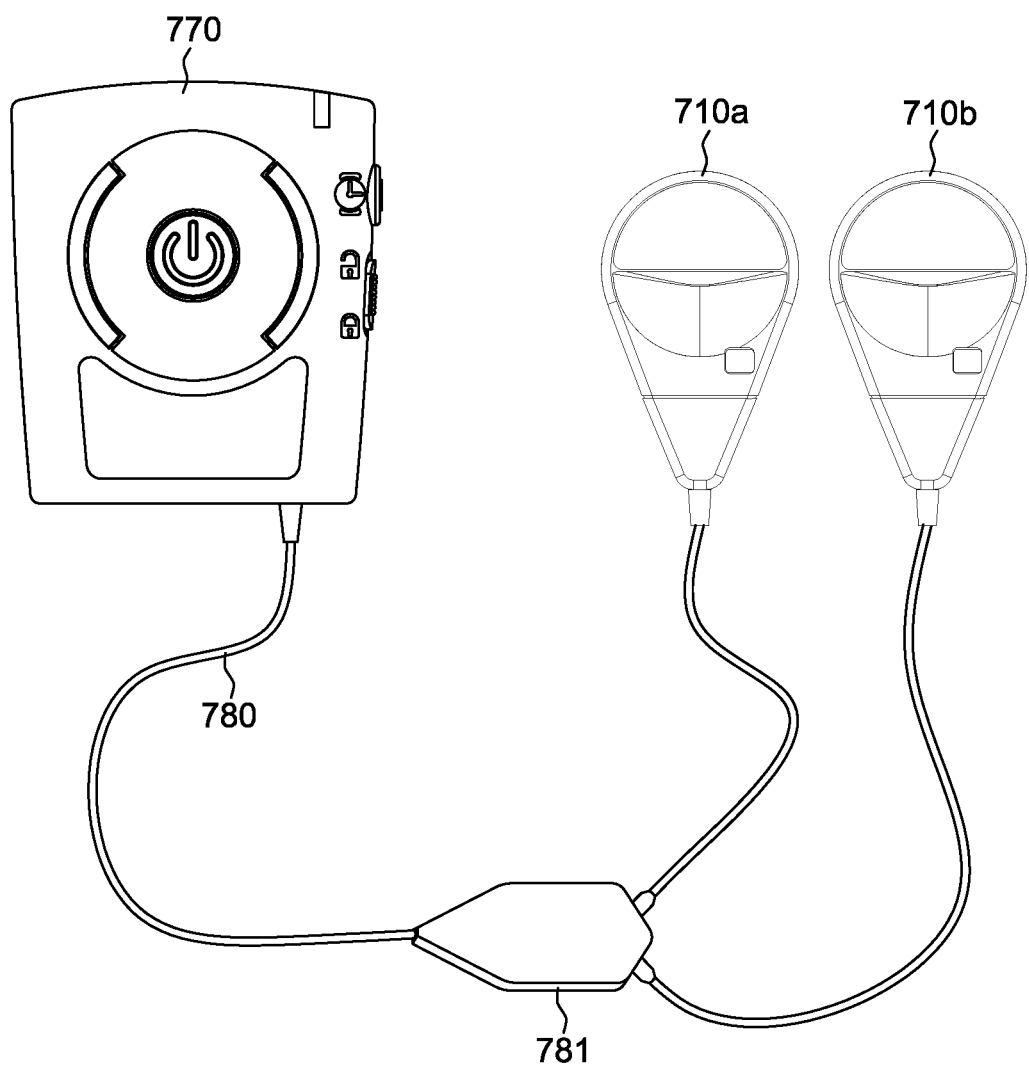
FIG. 7 depicts aspects of an embodiment of the present invention.

In an embodiment of the present invention where each individual applicator can collect this information and adjust ultrasound application based on this information, the individual applicators can also share information between them in order to adjust the overall treatment being received by the wearer. The activity of one applicator may influence the treatment administered by another applicator. In an embodiment of the present invention, a power controller 170 powers two or more applicators 110 for example, to illicit deep therapeutic effects. Each applicator 110 receives information from the applicators (e.g., skin temperature, applicator temperature, pulse oximetry, and/or other biometric information) and changes the control sequence or ultrasonic drive signals based on this information. As will be discussed later and as seen in FIG. 7, the individual applicators are electrically connected to each other with a "Y" adapter cable 781, which connects the applicators 710a-710b to a cable from the power controller 770 to connect to two or more applicators 710a-710b simultaneously. Thus, as the applicators are electrically coupled, the information collected by each applicator is accessible to the other applicators, such that a first applicator 710a can alter its ultrasound application based on the information collected by another applicator 710b.

An applicator 110 in an embodiment of the present invention may also include an acoustic spectroscopy sensor to measure sonic emissions from joints, tendons, ligaments, muscles and body tissues. This information can be utilized to alert a user to change in condition of the wearer to manually adjust treatment and/or can be used by control mechanisms in the applicator to adjust the treatment parameters. In an embodiment of the present invention, the applicator 110 may actively pulse a transducer and measure the echogenicity coming back and see changes over hours, days, weeks, providing feedback on the changing echogenicity, including real-time feedback to user, for example, by displaying in simple format on a display on the applicator 110 (LED, LCD), and/or retaining the data in a memory in the applicator 110, such that it can be optionally downloaded off system utilizing a connection, such as a USB port.

In an embodiment of the present invention with more than one applicator, such as seen in FIG. 7, one applicator 710a can be utilized to collect biometric information, while another applicator 710b is used to administer ultrasound treatment. For example, an applicator 710a can record mechanical elastography by monitoring shear waves with an integrated receiving transducer (not pictured). In another embodiment of the present invention, an applicator can include more than one transducer, including both transmitting and receiving transducers. In another example, one applicator 710a can be utilized to collect information on echogenicity, as described earlier, while the second transducer 710b is used to administer ultrasound at a different frequency.

In a further embodiment, the first applicator (710a) further comprises a proximity sensor to sense the location of the second applicator (710b).

In a further embodiment of the present invention, adjustment of controlling sequences for one or more applicators may be centralized to a common controller. This controller would obtain information from individual applicators and adjust control sequences for the individual applicators responsive to the collected information.

In an embodiment of the present invention, the common controller may comprise a memory to retain the collected information. In a further embodiment of the present invention, the individual controllers in the applicators may access either internal or external memory devices in order to retain the collected information.

In an embodiment of the present invention, more than one applicator coupled to the power controller can sense feedback from ultrasound transmissions, for example, utilizing a receiving transducer integrated into the applicator, to determine the location of one applicator relative to another applicator. This feature improves the quality of the treatment because a given applicator can determine whether it is too close to another applicator for effective therapy. In the case that one applicator is too close to another, the feedback to the transducer can trigger an alert, such as a sound, movement, or visual cue (e.g., light) from the applicator.

As aforementioned, embodiments of the present invention include a power controller 170, which can be controlled by one or more integrated circuits (ICs). The power controller 170 provides user control of the device and delivers electrical power to the applicator(s) 110 with controlled, stable amplitude, for a defined period of time. Aspects of the power controller 170 also enable the user to select treatment duration and provide user feedback.

Figure 2:
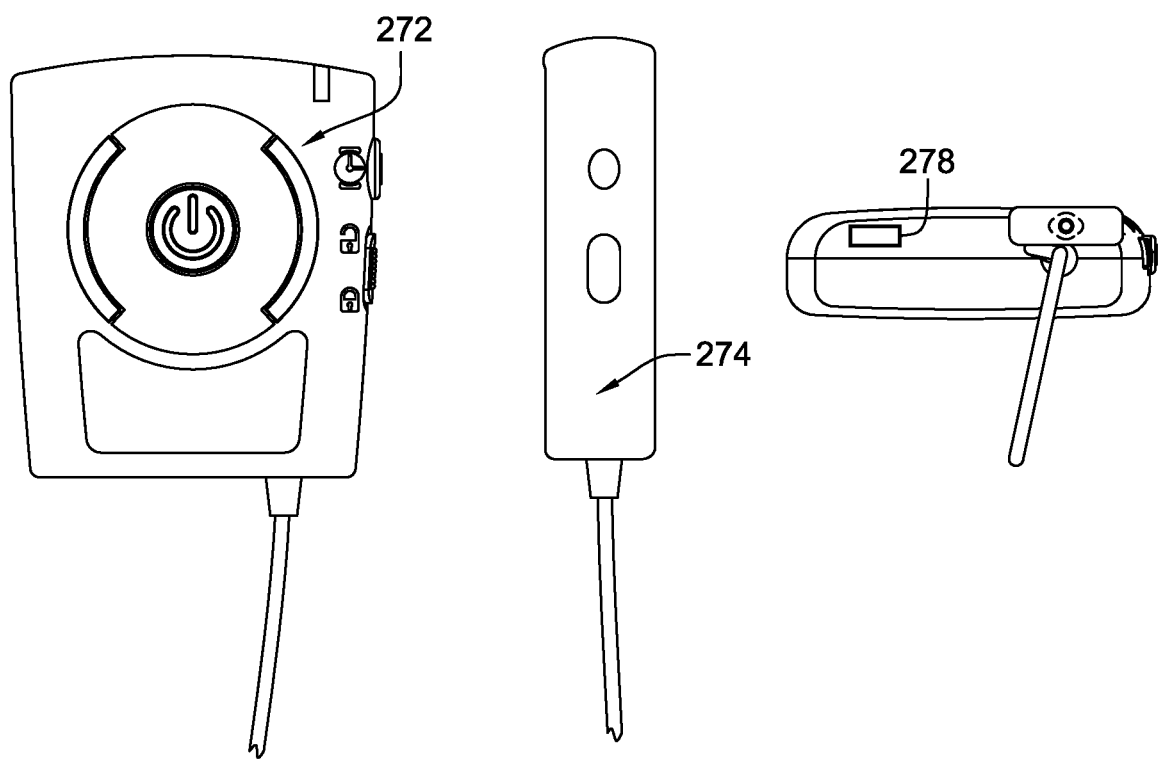
FIG. 2 depicts aspects of a power controller of an embodiment of the present invention.

FIG. 2 illustrates some aspects of an embodiment of the power controller 270. The power controller 270 provides power to the one or more applicators. In an embodiment of the present invention, the controller 270 provides power to more than one applicator simultaneously. The power controller 270 may be coupled with a control, such as a switch, or an interface with capacitive touch features, which enables a user to select the length of the treatment. For ease of use, embodiments of the present invention may employ a toggle switch and thus, enable the user to select from a finite set of options, for example, 1, 2, 3, or 4 hour treatments. The controller 270 may further include a locking mechanism control, to prevent accidental device treatment time toggle, and/or a power switch. In an embodiment of the present invention, treatment time lengths may be modified by making changes to a timing circuit. In an embodiment of the present invention, the power controller 270 can be connected to any of one or more applicators, either simultaneously or individually, i.e., the power controller 270 is interchangeable with any applicator.

The power controller 270 may vary in size. In the embodiment of the FIG. 2, the power controller 270 includes a Light Emitting Diode (LED) display 272 and provides information to the operator about time of treatment and the status of the power source 274, which may be a battery. In an embodiment of the present invention, the power source 274 can include one or more rechargeable lithium ion batteries that are capable of providing 5 or more hours of therapy with two ultrasound applicators on a single charge.

In an embodiment of the present invention, the controller comprises a USB port 278 through which the power source can be recharged.

In a further embodiment of the present invention, the power source can be charged utilizing a wireless recharge capability, including but not limited to magnetic, inductive and/or other wireless.

Rather than recharging an integrated power source in a power controller 270, to supply power to the device, in an embodiment of the present invention, a detachable battery pack connects to the power controller 270 and can be disconnected when the charge is drained and replaced with a new battery pack that is charged.

In a further embodiment of the present invention, a power source, such as a battery, may be integrated into an applicator 110 instead of, or in addition to, the power controller 170 (the power controller 170 and an applicator 110 may also be integrated into a single housing), in this embodiment, the applicator power source can be charged through a USB plug, wirelessly, and/or with a charging cradle.

The power source 274 of an embodiment of the present invention can be a battery because embodiments of the present invention can operate both at a low impedance and at a low voltage. For example, embodiments of the present invention may have less than 1 ohm impedance from battery source 274 (in the power controller) to RF ultrasound drive signal (in the applicator). Further embodiments of the present invention may have impedance from one to five ohms.

Embodiments of the present invention may also utilize low voltages for operation. Not only can the power controller 270 utilize a low voltage power source 272, such as a battery that supplies less than or equal to 5V, but the circuitry does not boost this voltage. Thus, the drive signal in the applicator that drives the one or more transducers is less than the nominal voltage of the battery. The voltage of less than or equal to 5V is utilized as a non-limiting example, as embodiments of the present invention can operate at nominal voltages from power source to drive signal.

Returning to FIG. 2, the display 272 indicates when the system is enabled (e.g., lit) or disabled (e.g., not lit). The display 272 further includes a series of LEDs to indicate the remaining time of treatment. In this embodiment, a second series of LEDs 276 indicates the remaining power source (e.g., battery charge) of the device. In this embodiment of the present invention, as a safety feature, the ultrasound frequency and intensity settings are preset by the manufacturer to the specifications stated on the labeling and cannot be modified by the user.

In an embodiment of the present invention, the power controller 270 is responsible for timing the ultrasound administered by the device. The applicators can administer ultrasound in both continuous and/or pulsed mode, the power controller 270 can include user controls to direct the mode of treatment. In another embodiment of the present invention, the mode is controlled by the applicator. In an embodiment of the present invention, power emissions from the controller 270 to the ultrasonic applicators terminate automatically at the end of the preset time or manually by pressing an On/Off button. An aforementioned lock, in this embodiment, (e.g., a sliding lock switch) is accessible on an outside surface of the housing of the power controller 270 and prevents the treatment time from being altered while the lock switch is engaged.

Figure 3:
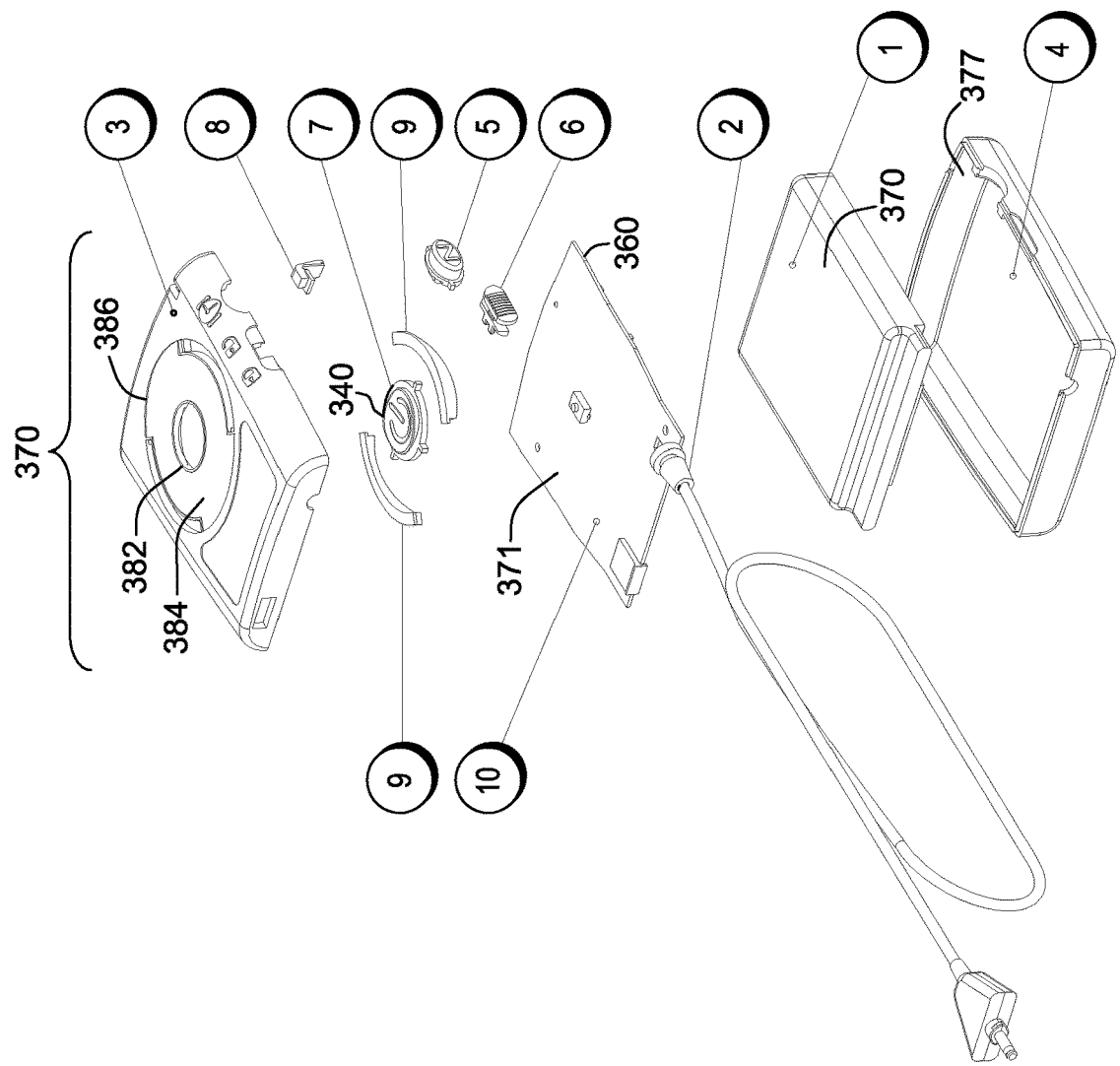
FIG. 3 depicts aspects of a power controller of an embodiment of the present invention.

FIG. 3 is an exploded view of the assembly of an embodiment of the power controller 370 of the present invention. In this embodiment, the power controller 370 does not include a microprocessor and/or firmware and/or or software on the device. However, additional embodiments may include these aspects as another means of controlling operation of an embodiment of the device.

Referring to FIG. 3, the power controller 370 includes a battery charge/protection/gauge stage 377 that supports the power source 379, in this embodiment, a lithium-polymer battery, for proper charge and discharging. The battery protection then goes through a fuel gauge measurement IC 382 that displays battery capacity to the user in a display 384, including, in an embodiment of the present invention, a series of LEDs 386. This gauge 377 is used to determine remaining battery capacity and the ability of the power controller 370 to provide the chosen treatment time by the user. In an embodiment of the present invention, the user is unable to select a treatment time that requires more power that is left in the battery.

To indicate the time that the device can be powered, in an embodiment of the present invention, an On/Off 340, treatment time selection 350, and lock switch 360 are interfaced with the timing circuit 371 and fuel gauge calculation. Once the device is powered on and the treatment time is selected, the timing circuit 371 counts down using an oscillator and series of dividers and counters (not pictured). In the embodiment of FIG. 3, remaining treatment time is indicated via an array of logic gates and series of LEDs 386. At the end of treatment the device powers down and a treatment completion light indication circuit is activated.

The individual components, including the electrical and mechanical components, that comprise an embodiment of the power controller include: a DC Power controller circuit board, a DC Power controller power source (including but not limited to a battery cell), a DC Power controller housing, DC Power controller labels, DC Power controller cable assembly.

Figure 11:
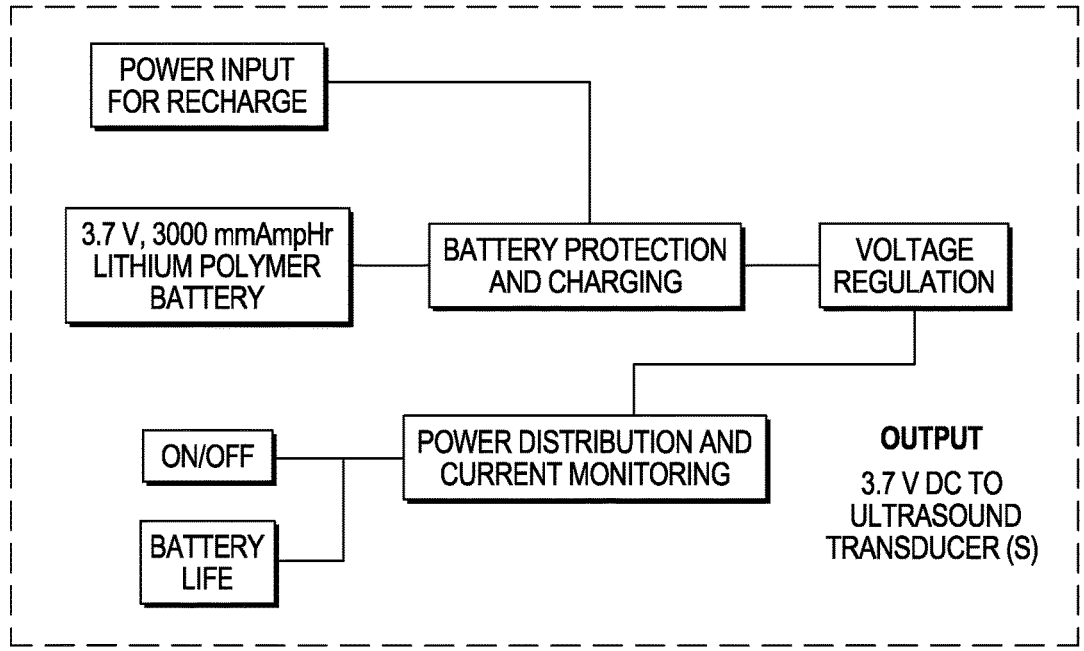
FIG. 11 is a functional block diagram of the board assembly design for a power controller of an embodiment of the present invention.

FIG. 11 is a functional block diagram of the board assembly design for a power controller of an embodiment of the present invention. Table 1 below is a list of qualities one or more of which may be utilized in various embodiments of the power controller of the present invention that are utilized with positive results in various embodiments of the present invention.

TABLE 1

| Aspects |
| --- |
| 3.7 +/− 5% VDC output signal |
| Battery pack with minimum 3000 mAHr rating |
| Power controller minimum 2 year shelf life |
| Battery full maximum charge time of less than 6 hrs |
| Minimum battery life cycle of 300 charge cycles |
| Tactile ON/OFF switch |
| User controls to select treatment time between 1 and 4 hours |
| USB compatible charger port |
| Indicator showing when the device is ON |
| Indicator showing when the device is in failure mode |
| Indicator showing when the device charging and when charged |
| LED Array indicating present battery life |
| LED Array showing therapy time remaining (in housing) |
| Accurate to 1 minute of actual remaining treatment time |
| Maximum treatment set time determined by battery power |
| Accessible lock switch disables other controls when device in use |
| LED indicator of treatment completion which remains on for greater than 4 hrs following treatment completion and subsequently turn off. |
| Compatible with IEC 60606-1 & 60601-1-2 |
| Power functions properly following a shake, rattle, roll test |
| Less than 2 cm in thickness |
| Usable over Commercial Temperature Range of 1° C.-44° C. |
| Cable assembly permanently connected to controller board |
| Locking male connector at the opposite end from controller board |
| Cable diameter 2.5 mm or less, wraps 10 times around a ¼" +/− ½₂" |

TABLE 1-continued

Figure 4:
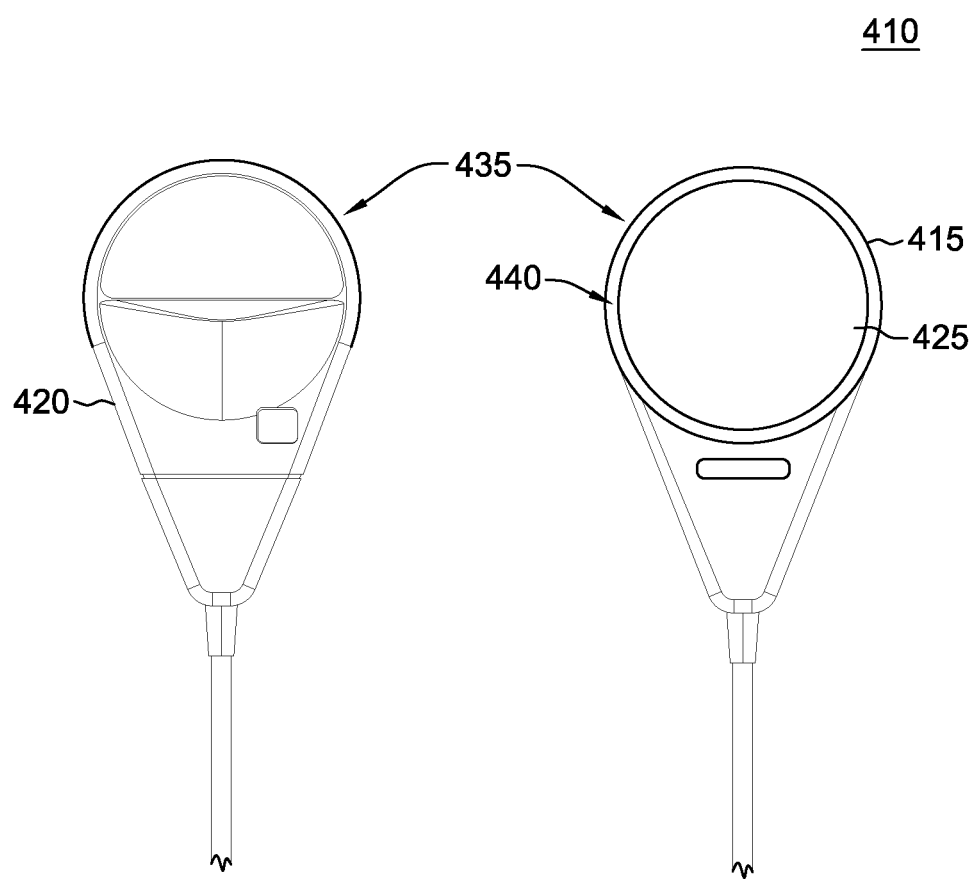
FIG. 4 depicts aspects of an applicator of an embodiment of the present invention.

Aspects rod with no damage, holds form when tied in a knot with 5 lbs of tension, and less than 3 ounces.
Cable rated for at least 700 mAmp of current
Main cable assembly 48 inches +/− 5% in length
Accessory cable with one (locking) female connector splitting to 2 with (locking) male connectors attached able to treat both sides of shoulder or both sides of knee concurrently
Cable assemblies shall be rated for 3.7 +/− 5% VDC
All locking connectors survive 500 mating cycles
All switches connections survive 1000 actuations
USB charging port survives 300 mating cycles
Voltage output maintains +/−20% line stability across treatment durations FIG. 4 illustrates an embodiment of an applicator, as described earlier, in reference to FIG. 1. Referring to FIG. 1, the applicator 110 converts the DC power signal delivered from the power controller 170 into a fixed frequency and amplitude ultrasound signal that can be transmitted into the body of the patient. As will be described in greater detail later, the applicator 110 is mated to the ultrasound bandage 130 and secured in place on the patient for the duration of therapy, and then reused with a new ultrasound coupling bandage, for subsequent therapy sessions. In an embodiment of the present invention, the coupling bandage 130 may maintain mechanical and ultrasound coupling between the applicator and individual. In an embodiment of the present invention, this coupling can be maintained for 0.5 or more hours.

Referring to FIG. 4, the depicted embodiment of the applicator 410 consists of a face 415 (e.g., 20 kHZ-40 MHz) with a diverging lens 425 (e.g., 0-90 degree) housed within an ABS plastic applicator 435 with interlocking/coupling lip 440. The examples given are non-limiting and describe a given embodiment. In various embodiments of the present invention, the shape of the lens 425 can vary. Although the embodiment of FIG. 4 utilizes a divergent lens, convergent and flat lenses are utilized in embodiments of the present invention in order to affect the application of the ultrasound. In various embodiments of the present invention, lenses utilized in applicator 410 may diverge, focus, and/or direct ultrasound.

The applicator 410 may also house the aforementioned ultrasound wave generator and temperature cutoff 420, current sensing and vibration notification integrated circuits. In an embodiment of the present invention, the dimensions of the applicator 410 are 1.52" L×1.30" W×0.45" H.

In an embodiment of the present invention, the lens 425 of the applicator 410, which can be convex curved, concave curved, and/or flat, may be made of medical grade Ultem material and/or a similar material. The front face lens circumference is surrounded by the interlocking lip 440 for the purpose of holding the applicator 410 to the coupling bandage 130. The interlocking lip 440, which may be comprised of plastic, also serves to offset the front face of the applicator 410 as a standoff so that the applicator 410 does not come in complete contact with the skin, even when using traditional ultrasound gel. In an embodiment of the present invention, applicator housing 435 and lens 425 are composed of medical grade ABS and Ultem plastics.

Applicator 410 includes an ultrasound wave generator (e.g., 20 kHZ-40 MHz, not pictured) that receives electrical energy from the power controller 470 and converts it into ultrasonic energy at one or more discrete continuous or pulsed ultrasonic output powers from each applicator 410. In some embodiments of the present invention, a display and/or alert indicate(s) that the device is emitting ultrasound. In one such embodiment, while actively emitting ultrasound, the applicator 410 displays a blue (lit) LED. As discussed earlier, if during operation, the applicator's 410 internal temperature increases in heat, as in the case of inappropriate coupling to the body, the thermal cutoff, which may comprise a temperature monitoring IC, will trigger (for example, at 51° C.±10%) and modulate the applicator 410 output, which may include disabling the applicator, while displaying an alert, for example, a red (lit) error LED, to the user. As an additional or alternate notification to a user, during overheating, the applicator 410 may incorporate a vibratory notification to notify the user of an error.

As an additional safety measure, in an embodiment of the present invention, after a failsafe trigger has occurred in the temperature monitoring IC, the applicator 410 can be re-enabled when the temperature drops below a pre-determined threshold, for example, 49° C.±10%. At or below this temperature the device will continue with its prescribed treatment unless canceled by the user or another failsafe trigger occurs.

In an embodiment of the present invention, the applicator incorporates a current measurement circuit to monitor energy being delivered to an ultrasound transducer for monitoring coupling and/or providing closed loop feedback on therapeutic energy being delivered. The closed-loop feedback monitors ultrasound coupling, ultrasound output power, ultrasound transducer and skin temperature, and modifies treatment accordingly to achieve maximum diathermy without causing skin burn or pain.

The applicator may also incorporate a heat sensor that monitors and controls ultrasound output to the patient to provide maximum diathermy without causing harm. The temperature monitoring allows various frequencies to be used from the applicator at various power settings.

To transmit ultrasound, the applicator may include one to multiple transducers of various resonances, to achieve multi-frequency therapies.

Figure 5:
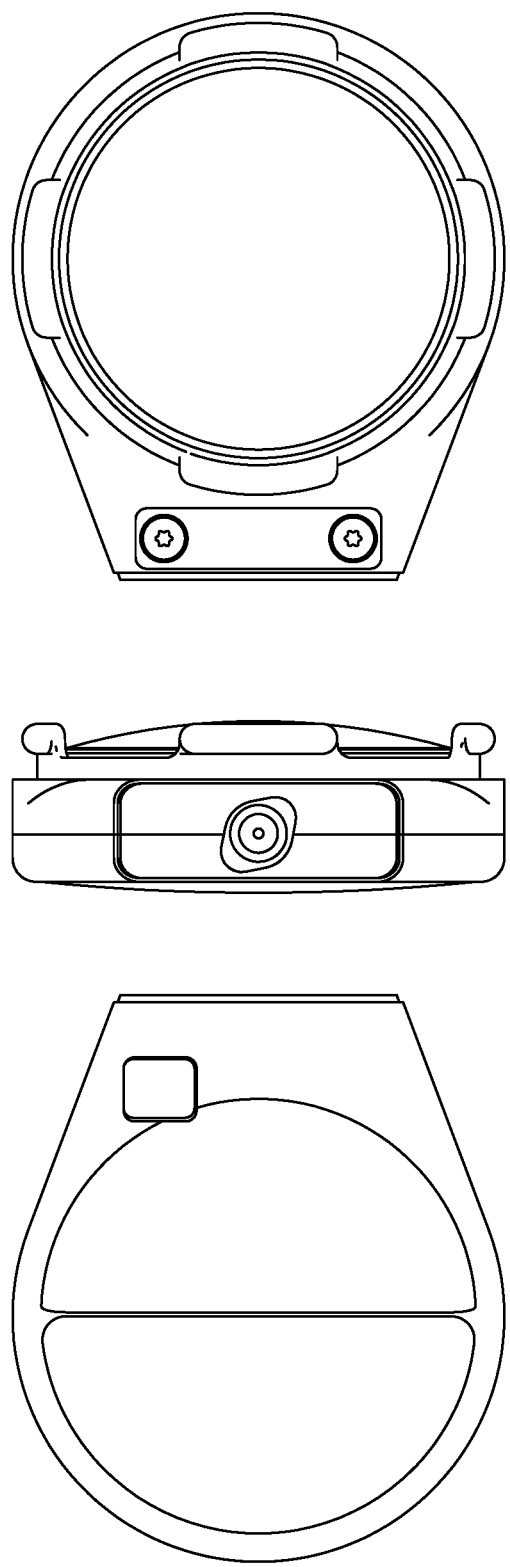
FIG. 5 depicts aspects of an applicator of an embodiment of the present invention.
Figure 6:
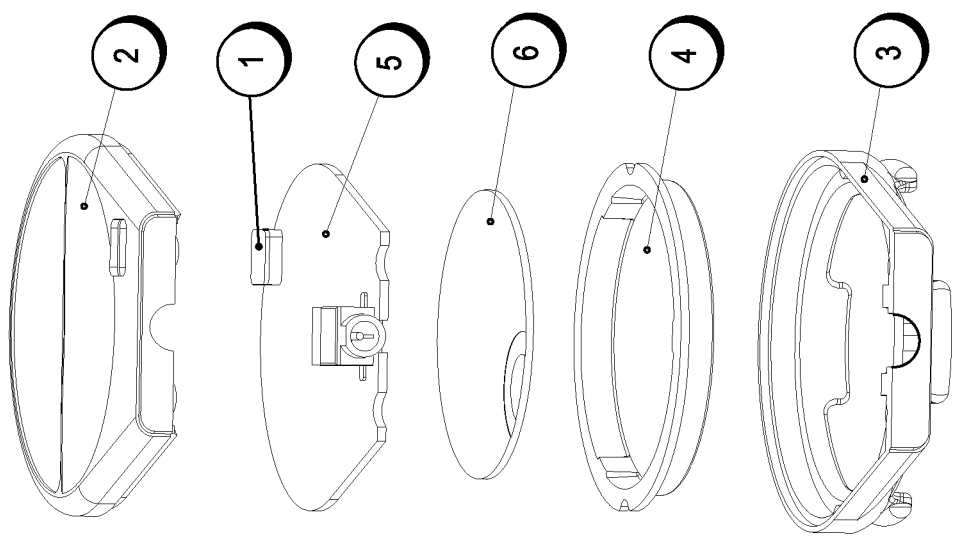
FIG. 6 depicts aspects of an applicator of an embodiment of the present invention.

FIGS. 5 and 6 include more detailed representations of the applicator of the present invention. As seen in these figures, applicator circuit consists of a DC-power jack, with fuse, which powers the clock oscillator at the appropriate frequency, which times the parallel pin-driver stage to powers one or more ultrasound transducers. A temperature and current monitoring IC controls power to the clock oscillator and error notification system, depending on the status of the device (active/non-active states). A series of timers are used to modulate the buzzer vibration in error mode. This embodiment does not include a microprocessor, firmware, and/or software on the device.

As seen in FIG. 5, the housing of the applicator has a custom 20-60 degree twist fit connector that prevents the wire from being pulled out when connected to the power controller. The connector on the housing may also incorporate a button release and other non-pull out mechanisms to assure the applicator is connected to the wire and that it does not disconnect when in use.

The applicator provides closed-loop diathermy control by monitoring heating, current, and output energy and adjusting it accordingly for the user of the device. All electronics and control of ultrasound output are on the applicator itself and it only receives DC power from the power controller. In other embodiments of the present invention, a battery pack is clipped in directly to the applicator to provide power.

Figure 12:
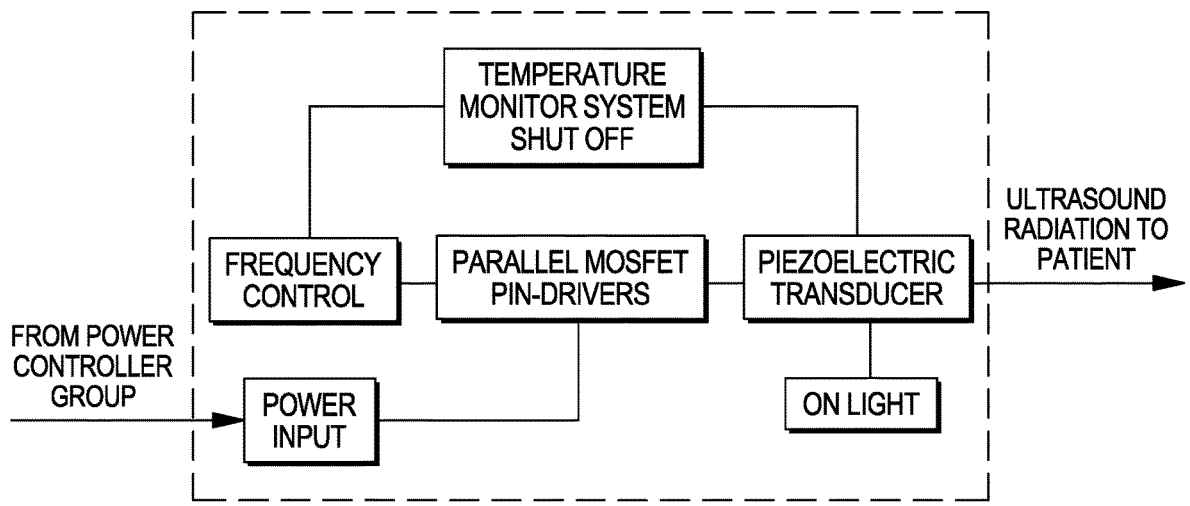
FIG. 12 is a block diagram of a board assembly design for an applicator utilized in an embodiment of the present invention.

As discussed prior, an embodiment of the applicator includes a board assembly, a housing assembly, a lens assembly, and labels. FIG. 12 is a block diagram of a board assembly design for the applicator.

Table 2 below is a list of qualities one or more of which may be utilized in various embodiments of the circuitry of the applicator, and other portions of the applicator, of the present invention, that produce positive results in various embodiments of the present invention.

TABLE 2

Aspects

A (locking) female connector mating with the (locking) male power controller cable connector for power input.
Input voltage of 3.7 +/− 20% VDC
Total acoustic power calibration will be 0.65 W +/− 20%
Calibration maintained at 0.65 W +/− 20% within 300 hours of use
Frequency: 3 MHz, +/−20%
No skin burn should result when using the applicator and bandage group combined.
Internal temperature cut off should prevent damage of applicator and user notification of overheating. The internal temperature of the device should cut off when it reaches 51° C.
Notification by LED will occur when the device is operational and when the device is in failure mode
PCB will fit within applicator housing specified later in this document, and be compatible with the applicator lens also specified in this document.
BNR (Beam non-uniformity ratio) will be less than 5:1
Piezoelectric elements in the ultrasound transducer have no contact points on the reverse side from lens, except for electrical connection points and thermal padding.
The applicator securely attaches to the reservoir (gel cup) of the ultrasound coupling bandage with 5 N or greater force for separation of the two parts.
Survive 300 attachment cycles to ultrasound coupling bandage
Lens design creates a 5 degree beam divergence, +/−20%.
Usable over commercial temperature ranges of 1-44° C. and 10-80% humidity.
Minimum 2 year shelf life.
When connected to the ultrasound coupling bandage, does not exceed 1.5 cm
Lens has 90% or greater contact with hydrogel when coupled to gel cup and in contact with the skin.
Detect whether or not there is appropriate coupling
Water resistant (front face)
Meets IEC 60601-1 & 60601-1-2 for electrical safety and electromagnetic radiation
Function properly following a shake, rattle, roll test Returning to FIG. 1, the applicator 110 (which can also be more than one applicator), is connected to the power controller 170. In this embodiment, a flexible power cable 180 is utilized to make this connection—one of skill in the art will recognize that this power cable 180 is merely one possible electrical connection as any standard electrical coupling known to one of skill in the art can be utilized in various embodiments of the present invention. FIG. 1 depicts an embodiment of the present invention utilizing a flexible power cable 180. In an embodiment of the present invention, the power cable 180 is locked into an applicator 110 with an interlocking mechanism in order to prevent any accidental uncoupling of these components.

Turning to FIG. 7, a flexible power cable 780 is utilized to connect two applicators 710a-710b to a power controller 770. In this embodiment, the power controller 770 is attached to a flexible power cable 780 that extends up to 4 feet in length. An additional "Y" adapter cable 781 is provided as an accessory that allows the single cable from the power controller 770 to connect to two or more applicators 710a-710b simultaneously. In an embodiment of the present invention, the Y-adapter cable 781 may split the 3.7V DC power into two parallel DC power sources that will interconnect with the applicators 710a-710b as well as the power cable 780 from the power controller 770. The Y-adapter couples more than one applicator 710a-710b to the same power source (in the power controller 770). In an embodiment of the present invention, the Y-adapter cable has digital signature to confirm association with the power controller 770 and each applicator 710a-710b.

In an embodiment of the present invention, the ends of each cable have integrated barrel connector plugs, which provide tactile snap-in feedback and a 30 degree twist fit mechanism, when appropriately connected together, which prevent the wire from inadvertently being un-plugged from the applicator 710a-710b.

As discussed in reference to FIG. 1, the coupling bandage 130 may be used to attach one or more applicators 110 to a wearer of the device. This adhesion enables a wearer to utilize the device in a hands-free manner. There are at least two additional advantages to utilizing the coupling bandage. First, the adhesive bandage provides a method of affixing a reservoir or gel cup, to the patient's skin. The reusable applicator, when mated with the gel cup, can be held reliably in a fixed position on the patient for the duration of treatment. Secondly, the gel cup filled with coupling media creates a low acoustic impedance pathway that optimally couples therapeutic ultrasound from the applicator into the patient's skin and underlying tissues. An embodiment of the ultrasound coupling bandage is a single use, disposable, consumable item that may be replaced with each therapy session.

In an embodiment of the present invention, the applicator 110 can be configured so that it cannot transmit ultrasound unless correctly coupled to the coupling bandage 130. Additionally, in an embodiment of the present invention, a timing circuit (not pictured) in the applicator 110 or other methods, including but not limited to RFID or other electronic tags, may monitor the duration of use of a given coupling bandage 130 and alert the user and/or shut off the applicator, when a given period has elapsed and therefore, the coupling bandage should be replaced for safety of use.

Figure 15:
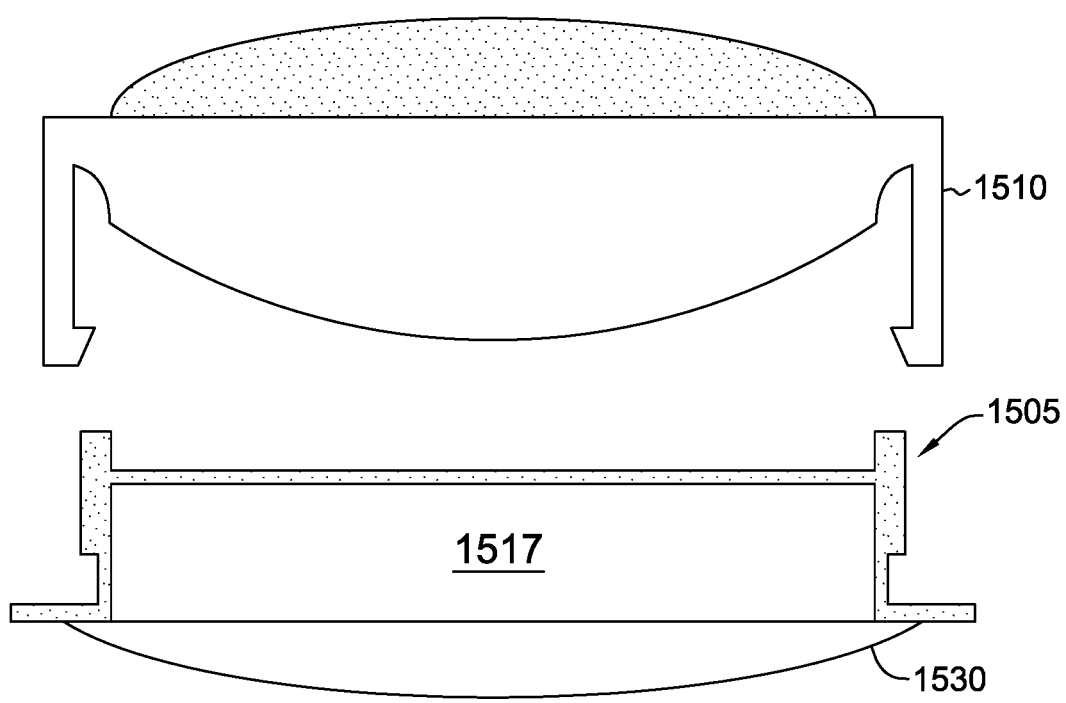
FIG. 15 illustrates how an embodiment of a coupling bandage and an embodiment of an applicator are coupled.

FIG. 15 illustrates how the coupling bandage and the applicator work together in the ultrasound device. In the cross section of FIG. 15, the gel cup 1505 of the coupling bandage 1530, which is filled with a coupling media (hydrogel) 1517, is positioned under a transducer 1513 in the applicator 1510. The coupling media (hydrogel) in the gel cup 1505 provides an acoustic pathway from the applicator 1510 group to the skin and underlying tissues. The resulting coupling media has equivalent acoustic impedance and transmission properties greater than 90% to that of commercially available ultrasound gels. Further, the coupling media 1517 deforms to form contact with at least 90% of the transducer lens surface when it is coupled to the gel cup 1505 and in contact with the skin. In an embodiment of the present invention, clipping the applicator 1510 over the hydrogel, removes air bubbles and/or air pockets in the hydrogel to applicator coupling.

Figure 8:
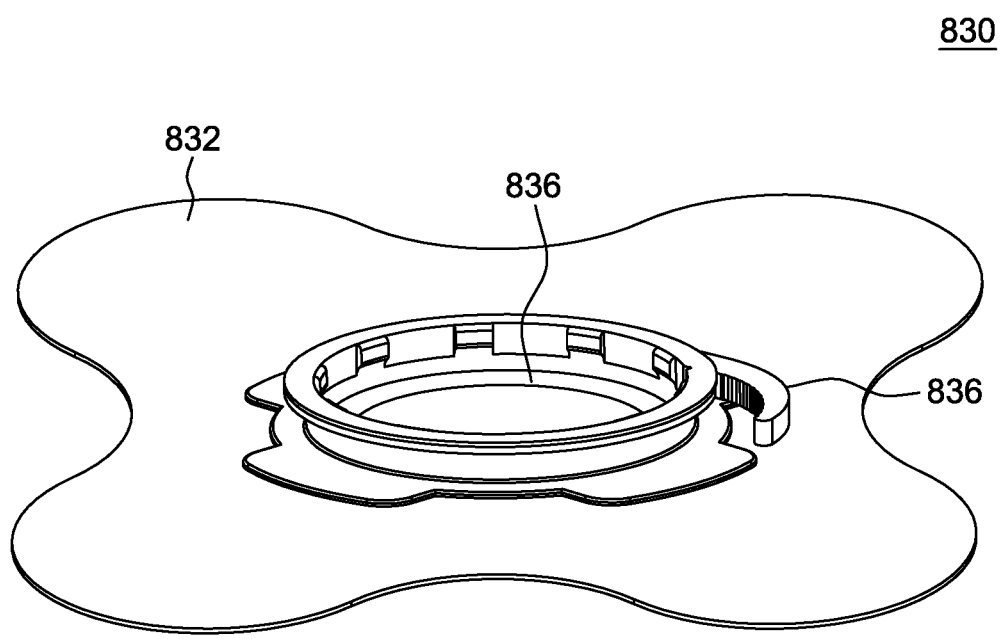
FIG. 8 depicts aspects of an embodiment of a coupling bandage.

FIG. 8 depicts aspects of an embodiment of a coupling bandage 130.

The wearable ultrasonic diathermy device of the present invention is configured for use with a coupling bandage 830. The coupling bandage 830 may be single use and adapted for less than 24 hours of surface contact. An embodiment of the coupling bandage 830 adheres to the body of a wearer of the ultrasound device because the coupling bandage 830 includes a polyester non-woven bandage material 832 (e.g., 4" L×4" W) to secure the bandage in place on the body. A central portion of the coupling bandage 830 includes a reservoir 836 that is filled, prior to application, including but not limited to, by the manufacturer, with a biocompatible hydrogel material similar to commercially available ultrasound coupling media. In an embodiment of the present invention, the hydrogel is 96% water, highly elastic, and deforms well to various skin surfaces to provide sufficient ultrasound coupling.

Figure 9:
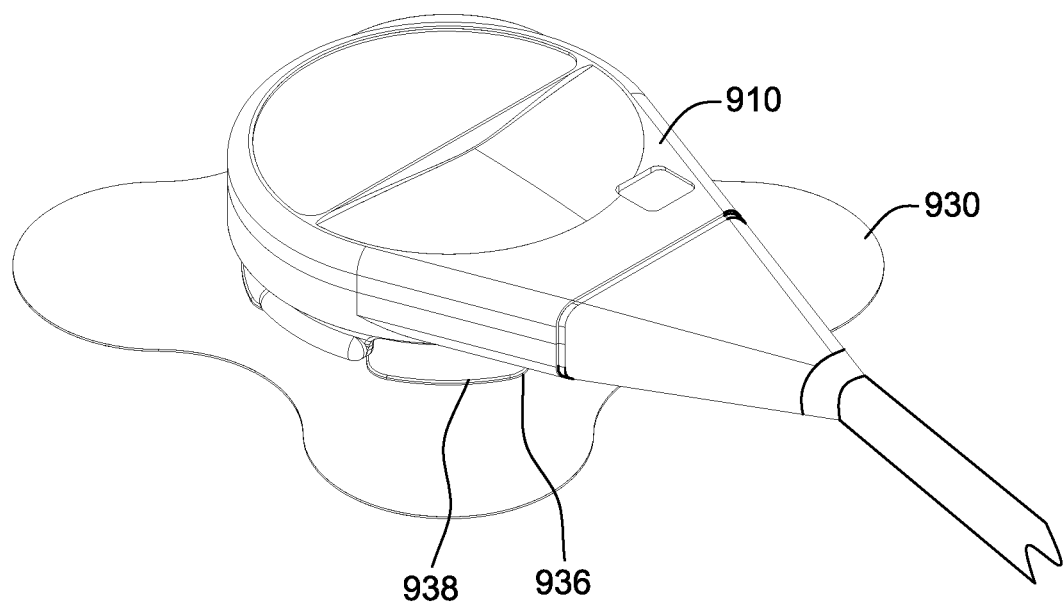
FIG. 9 depicts aspects of an embodiment of a coupling bandage.

Returning to FIG. 8, the (polypropylene) reservoir 836 connects with the lip on the applicator, to secure the applicator in place, as shown in FIG. 9.

Referring to FIG. 9, to remove the applicator 910, a tab 938 of the reservoir 936 (FIG. 8, 836) is pulled to break the reservoir 936 and allow the applicator 910 to be removed.

When utilizing embodiments of the present invention to provide long term ultrasound to a wearer, the applicator of the device is secured to a location on the body using a coupling bandage. The coupling bandage is designed specifically for use with the device. For example, in an embodiment of the present invention, a circular applicator connects to the center of the coupling bandage, as seen in FIG. 9.

Figure 10:
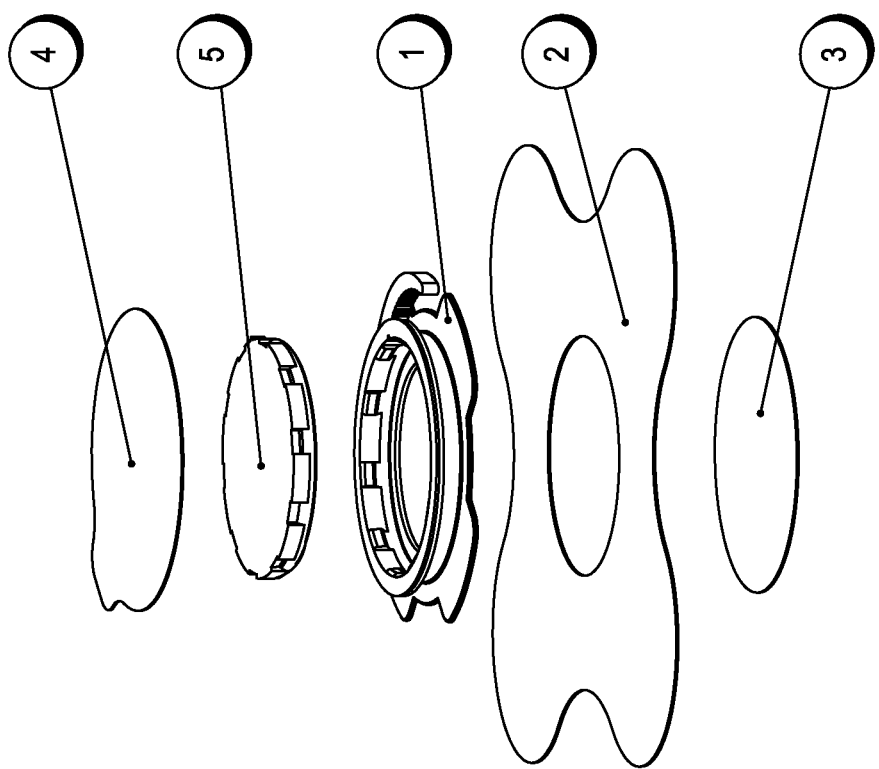
FIG. 10 is an exploded view of the elements of an embodiment of the coupling bandage.

FIG. 10 is an exploded view of the elements of an embodiment of the coupling bandage. In an embodiment of the present invention, the coupling bandages utilized are single use only and are not intended for use for more than one treatment session per bandage, and are classified for less than 24 hours of surface contact.

When used in the present invention, the coupling bandage provides substantially equivalent acoustic properties to commercially available ultrasound coupling gels. The coupling bandage provides efficient ultrasound coupling between the face of the applicator and a body surface.

An embodiment of the coupling bandage includes: a medical grade adhesive bandage, the aforementioned a reservoir (also referred to as a gel cup), coupling media, a bottom seal with adhesive coating, a top seal with polymer coating. The bandage geometry may be tailored to application on various anatomical regions. FIGS. 14A-14D depict the application of the device, utilizing the coupling bandage, to different parts of the body of a wearer.

As seen in 14D, the coupling bandage can be a wrap 1430. The wrap 1430 can vary in size and shape, or alternatively is a common size and shape or geared toward specific joints and areas of the body. An ultrasound coupling medium cartridge is placed inside the wrap or attached to the therapeutic ultrasound transducer. The applicator 1410, which includes the ultrasound transducer is then clipped into the wrap on pre-cut or movable ports.

Table 3 below is a list of qualities one or more of which may be present in various embodiments of the coupling bandage of the present invention. The aspects listed produce positive results in various embodiments of the present invention.

TABLE 3

Aspects

Maintain adhesion for at least 6 hrs during routine daily activities and on hairy skin.
Adhesive is single use, degrades to 66% of the original strength if attempted to be used 3 or more times in 4 hour intervals.
High dermatological tolerance based on 6 hour, 7 day use cycle.
Coupling media transmits ultrasound to within 90% or better in amplitude compared to predicate hydrogels and gel pads.
Pass Cytotoxicity (AAMI/ANSI/ISO 10993-5), Primary Skin Irritation (ISO 10993-10), and Sensitivity (10993-10) testing.
The gel cup when connected to an applicator enables the hydrogel to have >80% contact with skin surface.
Applicator lens has at least 90% contact with hydrogel when coupled to gel cup and in contact with the skin.
Removal of the bandage group and/or separation of the applicator from the bandage group renders the bandage group unusable.
Coupling media does not need to be sterilized.
Bandage dimensions facilitate placement on at least the knee, elbow, ankle, wrist, shoulder, back, or hip.
Meets shake, rattle, roll test
Usable over temperature range 1° C.-44° C.
When connected to the applicator, does not exceed 1.5 cm.

Figure 13:
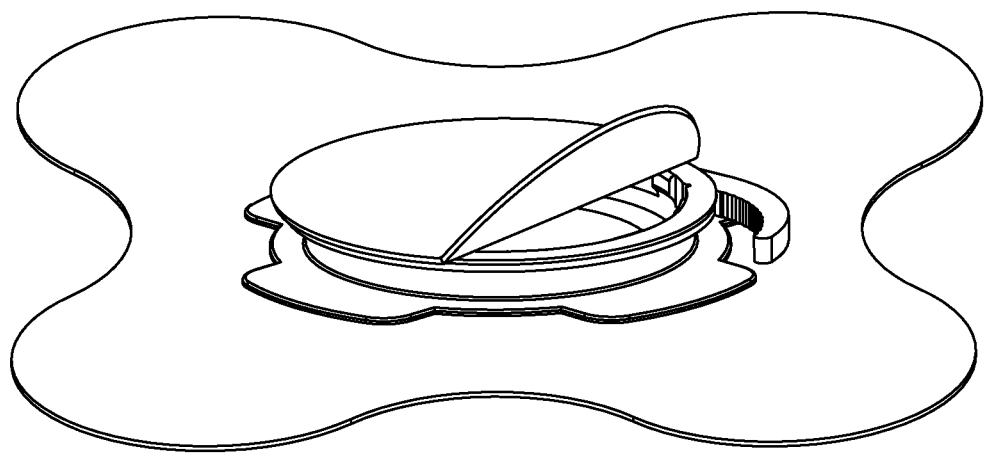
FIG. 13 depicts the removable seal of a coupling bandage of an embodiment of the present invention.
Figure 14A:
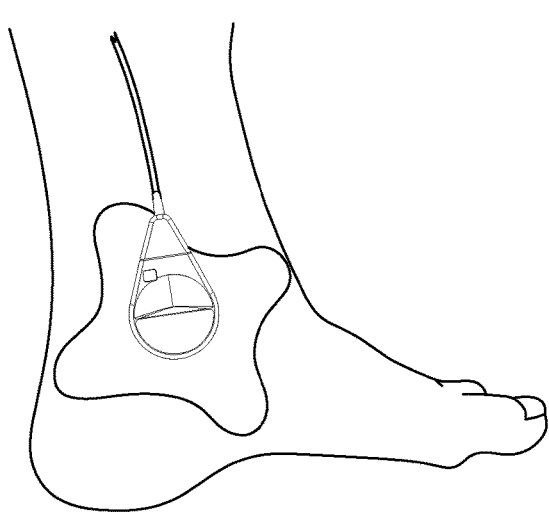
FIGS. 14A-14D each depict embodiments of coupling bandage of an embodiment of the present invention.
Figure 14B:
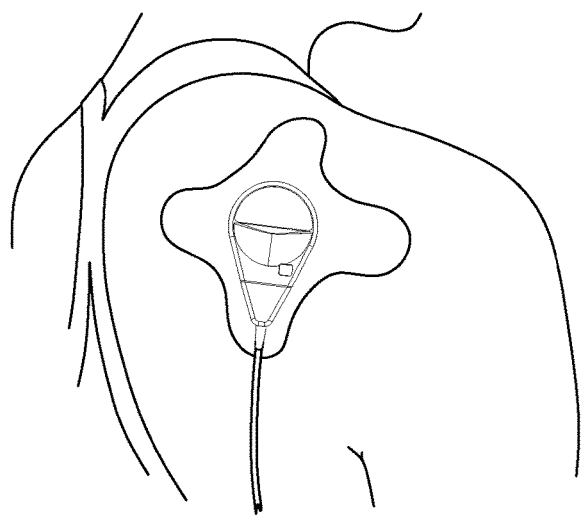
Figure 14C:
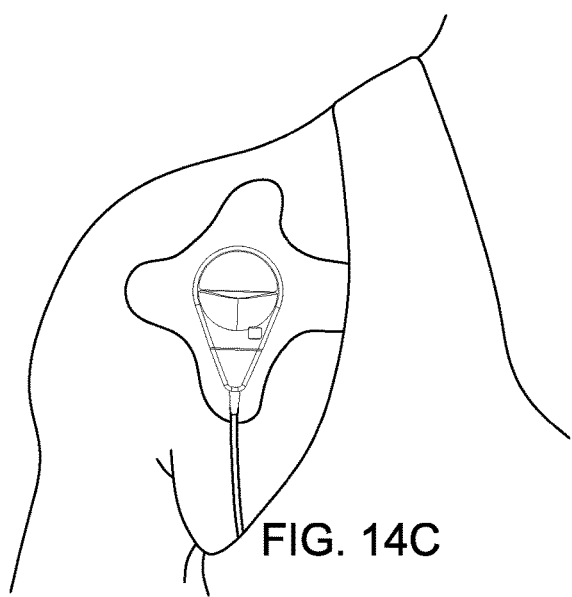
Figure 14D:
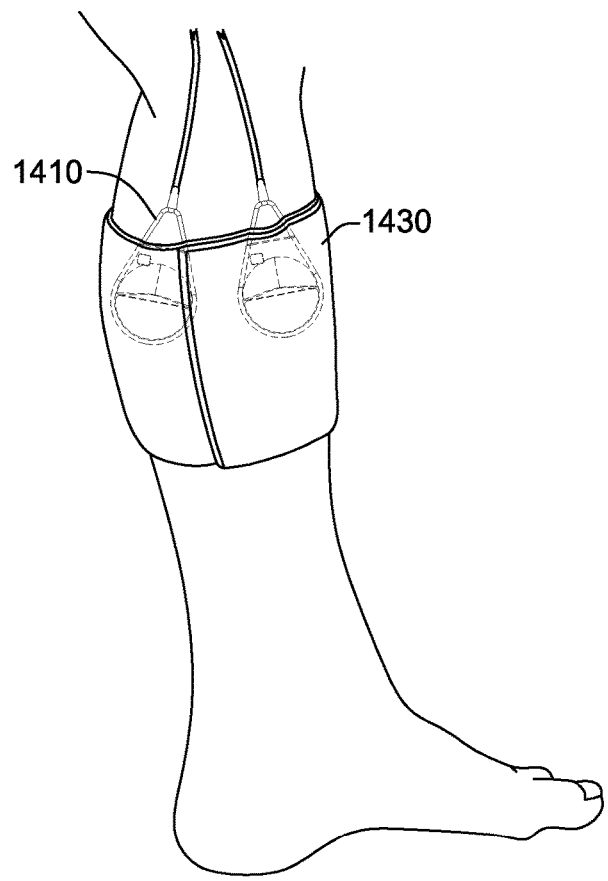

In an embodiment of the present invention, in order to preserve the usability of the coupling bandage before use, the reservoir may be fitted with a removable seal. This seal is depicted in FIG. 13. In an embodiment of the present invention, this seal may be removable above and below, may maintain integrity such that hydrogel remains viable for a 1 year shelf life and/or may have a burst strength of at least 30 psi as measured by ASTM F2054-07 or ASTM F2338-09.

The reservoir in the coupling bandage, also called the gel cup, may be made by injection molding from polypropylene, a material that is widely available, mechanically and chemically stable, low-cost, and in wide use in the medical device field.

Various aspects and embodiments of the present invention can utilize the low-profile ultrasound transducers, disclosed in U.S. Provisional Patent Application No. 61/838,768, filed Jun. 24, 2013, and International Application No. PCT/US2014/043951, entitled "LOW-PROFILE, LOW-FREQUENCY, AND LOW-IMPEDANCE BROAD-BAND ULTRASOUND TRANSDUCER AND METHODS THEREOF," filed on Jun. 24, 2014.

While several aspects of the present invention have been described and depicted herein, alternative aspects may be affected by those skilled in the art to accomplish the same objectives. Accordingly, it is intended by the appended claims to cover all such alternative aspects as fall within the true spirit and scope of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A wearable ultrasound device (100), comprising a power controller (170) comprising a power source (274) and at least one integrated circuit, wherein the power controller (170) delivers electrical power to a first applicator (110); the first applicator (110) electrically coupled to the power controller (170) by a flexible power cable (180), wherein the power controller (170) provides power at a stable Direct Current (DC) amplitude to the applicator (110), over a defined period of time or wherein the power controller (170) comprises user controls, wherein the controls enable the user to select treatment duration, wherein a surface of the first applicator (110) is adapted to transmit ultrasound to a wearer for a given duration, the first applicator (110) comprising: radio frequency (RF) drive electronics;
    a first ultrasound transducer coupled to the drive electronics;
    a first monitoring apparatus comprising a first thermal cutoff (120) coupled to the drive electronics, wherein the first monitoring apparatus monitors a temperature of the first applicator surface and the first thermal cutoff (120) turns off the first applicator (110), if the temperature exceeds a pre-defined threshold; the wearable ultrasound device (100) further comprising:
    a second applicator (710b) electrically coupled to the power controller (770), wherein the power controller (770) delivers electrical power simultaneously to the first applicator and the second applicator, wherein a second surface of the second applicator (710b) transmits ultrasound to a wearer for a given second duration, the second applicator (710b) comprising:
    second radio frequency (RF) drive electronics;
    a second ultrasound transducer coupled to the second drive electronics;
    a second monitoring apparatus coupled to the drive electronics, the second monitoring apparatus comprising a second thermal cutoff, wherein the second monitoring apparatus monitors a temperature of the second applicator surface and the thermal cutoff turns off the second applicator, if the temperature of the second applicator surface exceeds a pre-defined threshold; and
    a first coupling bandage (130) coupled to the first applicator (110) wherein the first bandage (130) positions the surface of the first applicator (110) proximate to a wearer at a first location on a body of the wearer and a second coupling bandage coupled to the second applicator, wherein the second bandage positions the second surface proximate to a wearer at a second location on the body of the wearer, wherein the location of the first applicator and the second location are not the same location and wherein the first applicator (710a) further comprises a proximity sensor to sense the location of the second applicator (710b), wherein the first monitoring apparatus further comprising at least one of: a sensor, or a receiving transducer, and wherein the monitoring apparatus 1s configured to obtain information related to the wearer or the applicator (110) and wherein the information comprises at least one of: skin temperature, applicator temperature, pulse oximetry, blood flow, blood oxygen content, mechanical elastography, sonic emissions, or biometric information, wherein based on obtaining the information, the RF drive electronics adjust a control sequence or ultrasonic drive signal of the first applicator (110), wherein the first applicator (110) comprises a housing (435) with a protrusion, wherein the first coupling bandage (130) is coupled to the first applicator (110) at the protrusion, comprising an interlocking lip (140).

2. The device of claim 1, wherein the first coupling bandage (130) is coupled to the first applicator (110) at the protrusion, comprising an interlocking lip (140) and the first coupling bandage (130) comprises a hydrogel reservoir (135), wherein the first applicator surface is in contact with the hydrogel reservoir (135), and wherein the hydrogel reservoir (135) is adapted to have a thickness to prevent the first applicator surface from coming into contact with skin of the wearer at the location.

3. The device of claim 1, the first applicator surface comprising a lens (425) coupled to the transducer, the lens (425) transmitting ultrasound from the transducer and wherein preferably the first coupling bandage (130) comprises a reservoir of hydrogel (135), wherein when the first coupling bandage (130) is applied to the location and coupled to the first applicator (110), the hydrogel is in contact with the lens (425), at least 90% thereof, and the location or the reservoir (135) maintains moisture between the lens (425) and the location.

4. The device of claim 1, wherein the power source (274):
    comprises at least one rechargeable battery, configured to provide 5 or more hours of therapy on a single charge, or
    comprises a low voltage battery, less than or equal to 5V, and the drive signal to the applicator is less than the voltage of the battery, or
    is removable and exchangeable with an equivalent power source.

5. The device of claim 1, wherein the power source (274) provides less than or equal to 1 ohm, between 1 ohm and 5 ohms, of impedance from the power source (274) to RF drive electronics.

6. The device of claim 1, wherein
    the first applicator (110) operates at two or more frequencies of operation,
    a shape of the first coupling bandage (130) is specific to the location,
    the device operates at a frequency of 20 kHz to 40 MHz, or
    a path from the power source (274) to the radio frequency (RF) drive electronics has low impedance, and a path from the radio frequency (RF) drive electronics to the transducer has low impedance.

7. The device of claim 1, wherein—the first applicator (710a) receives information via the ultrasound transducer of the first applicator (710*a*) concurrent with the second applicator (710*b*) transmitting ultrasound via the second transducer (710*b*) or the first applicator (710*a*) is adapted to transmit ultrasound at a first frequency and the second applicator (710*b*) is adapted to simultaneously transmit ultrasound at a second frequency and the first frequency and the second frequency are not the same, or a monitoring system of the first applicator (710*a*) further comprises at least one of: a sensor, or a receiving transducer, wherein the monitoring apparatus of the first applicator is configured to obtain information related to the wearer, and wherein the second applicator obtains the information from the monitoring system of the first applicator, or a first path from the power source (770) to the radio frequency (RF) drive electronics of the first applicator (710*a*) has low impedance, and a parallel path from the radio frequency (RF) drive electronics of the first applicator (710*a*) to the transducer of the first applicator (710*a*) has low impedance, and wherein a second path from the power source (770) to the second radio frequency (RF) drive electronics has low impedance, and a parallel path from the second radio frequency (RF) drive electronics to the second transducer (710*b*) has low impedance.

\* \* \* \* \*